United States Patent
Kohno et al.

(10) Patent No.: US 9,295,627 B2
(45) Date of Patent: Mar. 29, 2016

(54) MOUTHWASH COMPOSITION FOR PREVENTING AND/OR TREATING PERIODONTAL DISEASES

(71) Applicant: HAYASHIBARA CO., LTD., Okayama-shi, Okayama (JP)

(72) Inventors: Keizo Kohno, Okayama (JP); Emiko Ohashi, Okayama (JP); Tsunetaka Ohta, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 0 days.

(21) Appl. No.: 14/365,714

(22) PCT Filed: Dec. 12, 2012

(86) PCT No.: PCT/JP2012/082177
§ 371 (c)(1),
(2) Date: Jun. 16, 2014

(87) PCT Pub. No.: WO2013/089131
PCT Pub. Date: Jun. 20, 2013

(65) Prior Publication Data
US 2014/0356298 A1    Dec. 4, 2014

(30) Foreign Application Priority Data

Dec. 16, 2011   (JP) ................................. 2011-290574

(51) Int. Cl.
*A61K 8/60*      (2006.01)
*A61Q 11/00*     (2006.01)
*A23G 4/06*      (2006.01)
*A61Q 17/00*     (2006.01)

(52) U.S. Cl.
CPC . *A61K 8/602* (2013.01); *A23G 4/06* (2013.01); *A61K 8/606* (2013.01); *A61Q 11/00* (2013.01); *A61Q 17/005* (2013.01); *A61K 2800/30* (2013.01)

(58) Field of Classification Search
USPC .......................................................... 514/46
IPC ...................................................... A61K 35/64
See application file for complete search history.

(56) References Cited

U.S. PATENT DOCUMENTS

| | | |
|---|---|---|
| 4,948,783 A | 8/1990 | Kawai et al. |
| 5,102,873 A * | 4/1992 | Montgomery et al. .......... 514/46 |
| 2010/0168049 A1 | 7/2010 | Laboureau et al. |

FOREIGN PATENT DOCUMENTS

| | | |
|---|---|---|
| EP | 0066918 A1 | 12/1982 |
| JP | 58-41821 A | 3/1983 |
| JP | 60222411 A | 11/1985 |
| JP | 2004051515 A | 2/2004 |
| JP | 2005-314266 A | 11/2005 |
| JP | 2010155834 A | 7/2010 |
| JP | 2011032187 A | 2/2011 |
| WO | 03099297 A1 | 12/2003 |
| WO | 2011158904 A1 | 12/2011 |

OTHER PUBLICATIONS

David L. Cochran, "Inflammation and Bone Loss in Periodontal Disease", Journal of Periodontology, pp. 1569-1576, vol. 79, No. 8 (2008).
Schulze, A. et al. "Periodontal disease and heart disease", Clinical Sports Medicine International, pp. 9-12, vol. 1, No. 8, (2008).
Antonio Bascones-Martinez et al. "Periodontal disease and diabetes—Review of the literature" Medicina Oral Patologia Oral y Cirugia Bucal, pp. 722-729, vol. 16, No. 6 (2011).

* cited by examiner

*Primary Examiner* — Walter Webb
(74) *Attorney, Agent, or Firm* — Browdy and Neimark, P.L.L.C.

(57) ABSTRACT

The present invention has an object to provide a mouthwash composition for preventing and/or treating periodontal diseases safely and effectively. The present invention solves the above object by providing a mouthwash composition for preventing and/or treating periodontal diseases, characterized in that it comprises, as an effective ingredient(s), one or more members selected from the group consisting of adenosine N1-oxide, 3'-glucosyladenosine N1-oxide, 5'-glucosyladenosine N1-oxide, 5'-adenosine diphosphate N1-oxide, and 5'-adenosine triphosphate N1-oxide but does not contain any saccharide assimilable by periodontal disease bacteria.

5 Claims, No Drawings

MOUTHWASH COMPOSITION FOR PREVENTING AND/OR TREATING PERIODONTAL DISEASES

TECHNICAL FIELD

The present invention relates to a mouthwash composition for preventing and/or treating periodontal diseases.

BACKGROUND ART

Periodontal diseases are chronic inflammatory diseases inducible as a result of immunoreactions of living bodies against periodontal disease bacteria inhabited in dental plaques as biofilms formed around the teeth (see Non-Patent Literature 1). It has been well known that such periodontal diseases will induce not only the inflammation or the disruption of periodontal tissues but the absorption/destruction of bones for holding the teeth called alveolar bones, and finally cause the loss of the teeth.

Recent researches on the relationship between periodontal diseases and cardiovascular diseases point out that the former diseases possibly induce the latter diseases such as cardiac attack, cardiac infarct, and brain infarct through intravascular invasions of periodontal disease bacteria and their toxins through the gum to cause intravascular inflammation and induce the formation of thrombus (see Non-Patent Literature 2). It has been also said that toxins derived from periodontal disease bacteria may act on the liver and adipocytes, decrease the secretion of insulin to increase the blood sugar level, and result in raising the risk of diabetes-related complications. On the contrary, it has been also revealed that periodontal diseases and diabetes are closely related each other in that hyperglycemic state, for example, enhances the production of inflammatory cytokines and inflammatory mediators and promotes the disruption of periodontal tissues (see Non-Patent Literature 3).

As for the prevention and the treatment of periodontal diseases, there have been conventionally conducted, as the first choice, treatments for removing periodontal disease bacteria by plaque control and cleaning gingival sulcus and periodontal pockets. Such treatments, however, have restrictive effects on halting the progress of severe periodontal diseases. There have been also used antimicrobials for bacteriostasis and sterilization of periodontal disease bacteria, and used anti-inflammatories such as dipotassium glycyrrhizinate and tranexamic acid. Medicaments with more improved effects have been eagerly desired because the above-mentioned conventional antimicrobials and anti-inflammatories have been reported effective to treat periodontitis and gingivitis accompanied by the progress of periodontal diseases and to prevent unpleasant breath and ulorrhagia, but their effects still remain insufficient.

Patent Literature 1 discloses adenosine N1-oxide and its derivatives and related compounds, i.e., 1-N-hydroxyadenosine and 1-N-hydroxyadenosine-5'-phosphate; and also discloses that 1-N-hydroxyadenosine and 1-N-hydroxyadenosine-5'-phosphate can be used as neuromodulators due to their neuromodulatory actions. The term neuromodulatory actions as referred to in Patent Literature 1 means actions of protecting and activating neurocytes or satellite cells thereof, differentiating neurocytes, repairing the intracellular transfer system of neurocytes, repairing damaged neurocytes or satellite cells thereof, activating or inhibiting neurotransmission, and modifying actions of controlling the whole nervous system normally. Patent Literature 1 relates to a technology of the use of 1-N-hydroxyadenosine and 1-N-hydroxyadenosine-5'-phosphate as remedies for central nervous system diseases such as dementia, Alzheimer's disease, senile dementia, and dysautonomia; there exists no disclosure of the use of adenosine N1-oxide and derivatives thereof in any mouthwash composition for preventing and/or treating periodontal diseases that differ from the above-mentioned central nervous system diseases in terms of their causes, symptoms, etc.

Patent Literature 2 discloses adenosine and derivatives thereof, which can be formulated into cosmetic compositions and/or dermatological compositions based on the finding of their actions on minute skin asperity and on the stimulation of regenerating the dermis and/or the epidermis by stimulating the processes of cellular metabolism and epidermal regeneration, when used in combination with mannose or rhamnose. Accordingly, Patent Literature 2 relates to a technology on cares for the skin and/or the scalp by proliferating keratinocytes and fibroblasts with adenosine, derivatives thereof, or mixtures thereof that are used in combination with mannose or rhamnose. Patent Literature 2, however, never discloses the use of adenosine N1-oxide and derivatives thereof in any mouthwash composition for preventing and/or treating oral periodontal diseases that differ from the above-mentioned cares for the skin and/or the scalp in terms of their causes and symptoms, as well as targeted body parts.

Patent Literature 3 discloses aqueous royal jelly extracts fractionated as fractions with molecular weights of 2,000 or lower, which contain at least one member selected from compounds such as adenosine, adenosine N1-oxide, adenosine-5'-monophosphate, and adenosine-5'-monophosphate-N1-oxide; and orally ingestible osteoblast-proliferation inhibitors with any one of the above compounds. Such osteoblast-proliferation inhibitors are said, for example, to be used in preventing osteoporosis through the proliferation inhibition of a human osteoblast-like cell, i.e., MG63 (a pro-osteoblast cell), to promote the cell cycle from the proliferation cycle to the osteogenic differentiation (differentiation to osteoblast) cycle. Also, in Patent Literature 3, compounds which were confirmed to promote cell cycle from proliferation cycle to osteogenic differentiation cycle are only adenosine, adenosine-5-monophosphate, and adenosine-5'-monophosphate-N1-oxide; however, adenosine N1-oxide was not confirmed. Further, Patent Literature 3 never discloses that the adenosine N1-oxide and derivatives thereof usable in the present invention are used in mouthwash compositions for preventing and/or treating periodontal diseases.

Under these circumstances, there has been desired a medicament which effectively prevents and/or treats periodontal diseases that have been recently increasing in morbidity along with affected individuals among increasingly younger people.

PRIOR ART LITERATURES

Patent Literatures

[Patent Literature 1] Japanese Patent Kokai No. 2004-51515
[Patent Literature 2] Japanese Patent Kokai No. 2010-155834
[Patent Literature 3] Japanese Patent Kokai No. 2011-32187

Non-Patent Literatures

[Non-Patent Literature 1] "*Journal of Periodontology*", Vol. 79, No. 8, pp. 1569-1576, 2008
[Non-Patent Literature 2] "*Clinical Sportsmedsicine International*", Vol. 1, No. 8, pp. 9-12, 2008

[Non-Patent Literature 3] "*Medicina Oral Patologia Oral y Cirugia Bucal*", Vol. 16, No. 6, pp. 722-729, 2011

DISCLOSURE OF INVENTION

Object of the Invention

The present invention has an object to provide a mouthwash composition for preventing and/or treating periodontal diseases safely and effectively.

Means to Attain the Object

To attain the above object, the present inventors eagerly researched and found that adenosine N1-oxide and its derivatives including 3'-glucosyladenosine N1-oxide, 5'-glucosyladenosine N1-oxide, 5'-adenosine diphosphate N1-oxide, and 5'-adenosine triphosphate N1-oxide are useful as effective ingredients for a mouthwash composition for preventing and/or treating periodontal diseases. Thus, they accomplished the present invention.

The present invention solves the above object by providing a mouthwash composition for preventing and/or treating periodontal diseases, which contains one or more members selected from adenosine N1-oxide and derivatives thereof as an effective ingredient(s); more particularly, a mouthwash composition for preventing and/or treating periodontal diseases, characterized in that it contains, as an effective ingredient(s), one or more members selected from adenosine N1-oxide, 3'-glucosyladenosine N1-oxide, 5'-glucosyladenosine N1-oxide, 5'-adenosine diphosphate N1-oxide, and 5'-adenosine triphosphate N1-oxide but does not contain any saccharide assimilable by periodontal disease bacteria.

Effect of the Invention

The mouthwash composition for preventing and/or treating periodontal diseases of the present invention prevents and/or treats periodontal diseases effectively and safely. According to the mouthwash composition, unpleasant breath induced by periodontal diseases is also effectively improved as a merit. Further, according to the present mouthwash composition, the following are expected: the prevention of onset and the alleviation of cardiovascular diseases such as cardiac episode, cardiac infarct, and brain infarct, as well as diabetes and related diseases thereof, which all deeply relate to periodontal diseases.

BEST MODE FOR CARRYING OUT THE INVENTION

The mouthwash composition for preventing and/or treating periodontal diseases of the present invention is characterized in that it contains, as an effective ingredient(s), one or more members selected from adenosine N1-oxide, 3'-glucosyladenosine N1-oxide, 5'-glucosyladenosine N1-oxide, 5'-adenosine diphosphate N1-oxide, and 5'-adenosine triphosphate N1-oxide but does not contain any saccharide assimilable by periodontal disease bacteria. The term adenosine N1-oxide as referred to in the present invention means a compound registered as a CAS registry number of CAS No. 146-92-9 in "Chemical Abstract (CA)", an abstracting journal in the field of chemicals and their related fields published by Chemical Abstracts Service (CAS), a subsidiary organization of American Chemical Society (ACS). Examples of the derivatives of adenosine N1-oxide usable in the present invention include 3'-glucosyladenosine N1-oxide and 5'-gluosyladenosine N1-oxide as glycosides of adenosine N1-oxide, as well as 5'-adenosine diphosphate N1-oxide and 5'-adenosine triphosphate N1-oxide, etc., as phosphate compounds of adenosine N1-oxide.

The term "but does not contain any saccharide assimilable by periodontal disease bacteria" as referred to in the present invention means that the mouthwash composition of the present invention does not contain, as a carbon source, any saccharide easily assimilable/utilizable by periodontal disease bacteria for their growth: Saccharides such as glucose, fructose, maltose, sucrose, mannose, rhamnose, galactose, and xylose. Representative examples of the above periodontal disease bacteria include *Actinobacillus actinomyce temcomitans, Porphyromonas gingivalis, Prevotella intermedia, Bacteroides forsythus, Treponema denticola*, and *Tannella forsythensis*.

Explaining the adenosine N1-oxide and derivatives thereof used in the present invention, they may contain, for example, ingredients inherent to their production materials or side products formed during their synthetic processes as long as they do not depart from the object of the present invention. Desirable examples of the adenosine N1-oxide and derivatives thereof advantageously used in the present invention are those which have a highest possible purity, usually, those with a purity of 95% by mass (the term "% by mass" is simply abbreviated as "%" throughout the specification, unless specified otherwise) or higher, desirably, 98% or higher, and more desirably, 99% or higher. Preferable are those which do not substantially contain any microorganism and pyrogen in terms of safeness. When the adenosine N1-oxide and derivatives thereof usable in the present invention are commercially available, they can be arbitrary used intact or after purified with appropriate purification means used in this field, if necessary. The above adenosine N1-oxide and derivatives thereof can be obtained in a desired amount and at a satisfactorily yield, for example, by the synthetic methods as shown in the later Experiments 1 to 3, where adenosine or adenosine N1-oxide is used as a material.

The mouthwash composition for preventing and/or treating periodontal diseases of the present invention includes those which contain, as an effective ingredient(s), one or more members selected from adenosine N1-oxide and derivatives thereof in an amount of, usually, 0.01% or more, desirably, 0.1% or more but less than 10%, more desirably, 0.5 to 7.5%. When the amount departs from the lower limit of the above range, it would not be preferable because the effect of the present invention may not be entirely exerted or may be distinctly lowered. Although the upper limit of the amount of adenosine N1-oxide and derivatives thereof should not specifically be restricted, it should desirably be set in view of the solubilities of these compounds in media such as solvents for their dissolution.

The mouthwash composition for preventing and/or treating periodontal diseases of the present invention can be incorporated with any high intensity sweetener as a sweetener for sweetening to be easily orally used by users. Concrete examples of such sweetener include one or more of those which are generally used in this field: Saccharine, saccharine sodium, aspartame, acesulfam-K, sucralose, licorice extract, steviol glycoside, thaumatin, and glycyrrhizin. Further, saccharides such as glucose, fructose, maltose, sucrose, mannose, rhamnose, galactose, and xylose can be mentioned as sweeteners; however, as already mentioned, these saccharides should positively be eliminated in practicing the present invention because they are periodontal-disease-bacteria-assimilable saccharides having a fear of promoting the growth of periodontal disease bacteria and inducing or enhancing periodontal diseases. On the contrary, the above-identified high intensity sweeteners are free of the above-mentioned fear because they are not assimilated by periodontal disease bacteria and they can be suitably used as sweeteners for imparting sweetness to the mouthwash composition of the present invention. Further, varying depending on the kinds of the above-identified high intensity sweeteners, they are respectively incorporated into the mouthwash composition in an amount of 0.0001% or more, desirably, 0.001% or more but less than 10%, more desirably, 0.001 to 1%, and furthermore, 0.001 to 0.1% in terms of the total mass of the mouthwash composition.

The mouthwash composition for preventing and/or treating periodontal diseases of the present invention includes medicaments in a dosage unit form. Such medicaments mean those which contain one or more members selected from adenosine N1-oxide and derivatives thereof in an amount, for example, worth a daily dose, integral multiple aliquots thereof (up to 4-times), or divisors (up to ¼), in a physically separable dosage form suitable for oral administration/application. The timing for practicing oral washing with the mouthwash composition for preventing and/or treating periodontal diseases of the present invention is usually, preferably between or after meals.

The mouthwash composition for preventing and/or treating periodontal diseases of the present invention can be formed in combination with one or more of the following ingredients usually used in preparing pharmaceuticals and quasi-drugs: Oral abrasives such as calcium hydrogen phosphate, calcium carbonate, and silicic anhydride; foaming agents such as sodium lauryl sulfate and sodium lauroyl sarcosinate; binders such as alginate sodium; flavoring agents such as menthol, peppermint oil, and spearmint oil; preservatives such as paraben; surfactants such as sodium lauryl sulfate, sodium lauroyl sarcosinate, sorbitan fatty acid ester, polyoxyethylene sorbitan fatty acid ester, polyoxyethylene sorbitol fatty acid ester, polyoxyethylene fatty acid ester, polyoxyethylene higher aliphatic alcohol, polyoxyethylene allyl ether, polyoxyethylene lanolin derivative, polyoxyethylene lanolin alcohol derivative, polyoxyethylene castor oil derivative, polyoxypropylene polyoxyethylene cetyl alcohol ether, polyoxyethylene alkylphenol formaldehyde condensed derivatives, polyoxyethylene alkylamine, and polyoxyethylene alkylamide; fillers; bulking agents; excipients; binders; humectants; disintegrants; lubricants; physiologically acceptable solvents; and refined water or the likes. Varying depending on the kinds of the above-identified ingredients, they can be respectively incorporated in an amount of, usually, 0.0001% or more, desirably, 0.001% or more but less than 95%, more desirably, 0.01 to 50%, and furthermore, 0.1 to 10% with respect to the total mass of the mouthwash composition. When the mouthwash composition has the form of an oral pharmaceutical preparation, it can be selectively made into compositions with various forms depending on their purposes. Representative examples of such include mouthwashes, tooth pastes, tooth powders, chewing gum agents, troches, oral gel agents, intercalators for periodontal pockets, oral mucosa adhesive ointments, gingival adhesive tape preparations, oral dermatological magmas, oral dermatological pastes, oral balls, oral dispersants, oral powders, oral liquids, oral suspensions, oral emulsions, oral granules, and oral capsules. As preferred examples of the mouthwash composition for preventing and/or treating periodontal diseases of the present invention, those in the form of a liquid or paste can be most suitably used because of their readily handleability.

When formed into, for example, those in the form of an oral gel agent, intercalator for periodontal pocket, oral mucosa adhesive ointment, gingival adhesive tape preparation, or oral dermatological magma, the mouthwash composition for preventing and/or treating periodontal diseases of the present invention can be formed in combination with one or more members selected from lower alkyl ether compounds; vinyl compounds such as polyvinyl pyrrolidone, polyvinyl alcohols, and carboxy vinyl polymers; high molecular polyethylene glycols; polyacrylamides; polyoxyalkylenes such as polyethylene oxide; alginic acid and salts thereof such as sodium alginate and ammonium alginate; methacrylic acid and salts thereof; copolymers of styrene- and vinyl-type ether monomers, and salts thereof; polypeptides; higher fatty acids such as stearic acid and palmitic acid; surfactants with an HBL from 1 to 8; inorganic powders such as titanium oxide; white petrolatum; collagen; petrolatum; and atelocollagen. Varying depending on the kinds of the above ingredients, the incorporation amount of anyone of which is usually set to 0.0001% or more, desirably, 0.001% or more but less than 95%, more desirably, 0.01 to 50%, and furthermore desirably, 0.1 to 10%, in terms of the total mass of the mouthwash composition.

In the case of forming the mouthwash composition for preventing and/or treating periodontal diseases of the present invention into those in the form of a troche, the mouthwash composition can be formed in combination with one or more members selected from the following carriers used in the art: Excipients such as sodium chloride, urea, calcium carbonate, kaolin, and silicic acid; binders such as water, ethanol, propanol, shellac, calcium phosphate, and polyvinyl pyrrolidone; disintegrants such as sodium alginate, agar, laminaran powder, sodium hydrogen carbonate, calcium carbonate, polyoxyethylene sorbitan fatty acid esters, sodium lauryl sulfate, and stearic acid monoglyceride; disintegration inhibitors such as stearic acid, cacao butter, and hydrogenated oil; absorption promoters such as quaternary ammonium salts and sodium lauryl sulfate; humectants such as glycerin; adsorbents such as kaolin, bentonite, and colloidal silicic acid; and lubricants such as purified talc, stearate, and boric acid. In the case of forming the mouthwash composition for preventing and/or treating periodontal diseases of the present invention into those in the form of an oral ball, those which are known as carriers in the art can be arbitrarily used: Excipients such as cacao oil, hydrogenated vegetable oil, kaolin, and talc; binders such as ethanol and water; and disintegrants such as laminaran and agar. Varying depending on the kinds of the above ingredients, the incorporation amount of any one of which is usually set to 0.0001% or more, desirably, 0.001% or more but less than 95%, more desirably, 0.01 to 50%, and furthermore desirably, 0.01 to 10% in terms of the total mass of the mouthwash composition.

Other ingredients except for the above-identified ingredients can be incorporated into the mouthwash composition for preventing and/or treating periodontal diseases of the present invention. As described above, since saccharides such as glucose, fructose, maltose, sucrose, mannose, rhamnose, galactose, and xylose are assimilable by periodontal disease bacteria, they are anxious about promoting the growth of periodontal disease bacteria to induce or enhance periodontal diseases. Thus, such saccharides should positively be eliminated in practicing the present invention. Further, the mouthwash composition for preventing and/or treating periodontal diseases of the present invention should desirably do not contain any natural extracts such as plant and royal jelly extracts that potentially induce or promote periodontal tissue inflammations and allergic reactions.

Examples of the above-mentioned other ingredients include tranexamic acid, tranexamic acid hydrochloride, dipotassium glycyrrhizinate, β-glycyrrhetinic acid, dihydrocholesterol, minocycline hydrochloride, chlorhexidine, chlorhexidine hydrochloride, phenolic compounds (including thymol, methyl salicylate, and catechin), povidone-iodine, benzalkonium chloride, cetylpyridinium chloride, cetylpyridinium chloride hydrate, alkyl di(aminoethyl)glycin, dequalinium chloride, lysozyme hydrochloride, tocopherol hydrochloride, sodium azulene sulfonate hydrate, triclosan, allantoin, allantoin chlorohydroxy aluminum, and calcium salts (including monocalcium phosphate, dicalcium phosphate, and tribasic calcium phosphate), one or more of which can be appropriately used in combination. Varying depending on the kinds of the above ingredients, the incorporation amount of any one of which is usually set to 0.0001% or more, desirably, 0.001% or more but less than 10%, more desirably, 0.001 to 1% in terms of the total mass of the mouthwash composition.

The present invention is explained in detail with reference to the following Experiments: Experiments 1 to 3 show examples of producing the adenosine N1-oxide and derivatives thereof used in the present invention, and Experiment 4 shows that these adenosine N1-oxide and derivatives thereof are safe substances administrable to humans. Experiments 5 and 6 show volunteer tests with these substances.

Experiment 1

Preparation of Adenosine N1-Oxide

Twenty grams of adenosine with a product code of A9251-25G, commercialized by Sigma-Aldrich Japan K.K., Tokyo, Japan, was dispersed in one liter of acetic acid and admixed with 100 mL of 30% hydrogen peroxide solution, followed by stirring the resulting mixture at ambient temperature for five days. An excessive amount of the remaining hydrogen peroxide was decomposed by the addition of five grams of 5% palladium carbon, commercialized by Kawaken Fine Chemicals Co., Ltd., Tokyo, Japan, followed by filtering the mixture to remove the palladium carbon, drying the resulting solution in vacuo, adding ethanol to the dried product to disperse the formed crystals, and filtering the resulting mixture to obtain crude crystals of adenosine N1-oxide. Eight grams of adenosine N1-oxide with a purity of 99.5% was obtained by dissolving the crude crystals in ethanol by heating, filtering the resulting solution, ice-chilling the filtrate to effect recrystallization, and repeating these steps twice.

Experiment 2

Preparation 1 of a Derivative of Adenosine N1-Oxide

A cyclomaltodextrin glucanotransferase derived from *Geobacillus stearothermophilus* Tc-91 strain, which had been deposited in International Patent Organism Depositary, National Institute of Advanced Industrial Science and Technology, Higashi 1-1-1, Chuo-6, Tsukuba-shi, Ibaraki, Japan, under the accession number of FERM BP-11273, was allowed to act on an aqueous solution containing 5% of adenosine with a product code of A9251-25G, commercialized by Sigma-Aldrich Japan K.K., Tokyo, Japan, and 20% dextrin at pH 5.5 and 50° C. for 45 hours. The resulting mixture was admixed with 20,000 units/g of "GLUCOZYME #20000", a product name of a glucoamylase, commercialized by Nagase ChemteX Corporation (NCX), Osaka, Japan, and subjected to an enzymatic reaction at pH 4.5 and 50° C. for 24 hours. The resulting enzymatic reaction solution was purified on column chromatography to obtain 3'-glucosyl adenosine and 5'-glucosyl adenosine with a purity of 98% or higher. Similarly as in Experiment 1, the above 3'- or 5'-glucosyl adenosine was oxidized with a hydrogen peroxide solution and purified on column chromatography using "YMC-Pack R & D ODS-A Column", a product name of a reverse phase column, commercialized by YMC Co., Ltd., Tokyo, Japan, to obtain 3'-glucosyladenosine N1-oxide and 5'-glucosyladenosine N1-oxide with a purity of 98% or higher.

Experiment 3

Preparation 2 of a Derivative of Adenosine N1-Oxide

To a 500 mL four-necked flask were added 8.54 g of adenosine 5'-diphosphate with a product code of 590-29413, commercialized by Wako Pure Chemical Industry, Ltd., Osaka, Japan, 28 mL of refined water, and 84 mL of acetic acid. While stirring at ambient temperature, the resulting mixture was then added with 28 mL of 30% hydrogen peroxide solution over two minutes, and further stirred at ambient temperature for 13 days. Thereafter, the resulting mixture was admixed with 280 mL of acetone over 20 min under ice-chilling conditions, and further stirred for one hour. The resulting reaction product was collected by suction filtration and washed with 40 mL of acetone, followed by drying the resulting solids in vacuo in a desiccator. Then, 5.8 g of the solids was dissolved in 20 mL of water and admixed with 116 mL of acetone to effect crystallization. The obtained crystals were collected by suction filtration to obtain 4.76 g of 5'-adenosine diphosphate N1-oxide, which was then purified on column chromatography to obtain 5'-adenosine diphosphate N1-oxide with a purity of 98% or higher.

5'-Adenosine triphosphate N1-oxide with a purity of 98% or higher was obtained similarly as in the above procedure except for replacing the above adenosine 5'-diphosphate with adenosine 5'-triphosphate with a product code of P0756L, commercialized by New England Biolabs Japan Inc., Tokyo, Japan.

Experiment 4

Acute Toxicity Test

Two grams of any one of the adenosine N1-oxide obtained in Experiment 1, the 3'-glucosyladesonine N1-oxide and 5'-glucosyladenosine N1-oxide obtained in Experiment 2, and the 5'-adenosine diphosphate N1-oxide and 5'-adenosine triphosphate N1-oxide obtained in Experiment 3 was dissolved in 100 mL of D-PBS (Dulbecco's Phosphate-Buffered Salines). The resulting solution was intraperitoneally administered to 10 BALB/c female mice, six-week-old, with an average body mass of 20 g each, commercialized by Charles River Laboratories Japan, Inc., Kanagawa, Japan, at a dose of one milliliter/head, followed by observation for 24 hours. As a control, only D-PBS was intraperitoneally administered to 10 BALB/c female mice, six-week-old, with an average body mass of 20 g each, commercialized by Charles River Laboratories Japan, Inc., Kanagawa, Japan, at a dose of one milliliter/head, followed by observation for 24 hours. Thereafter, each mouse was collected her blood and urine for measuring clinical test items as indexes for renal and liver functions. Neither any apparent change was observed in any mice with any one of the test compounds from just after the administration to the termination of the observation, nor observed any difference between the values for the clinical test items of the test mice and those of the control mice. As a result, adenosine N1-oxide, 3'-glucosyladenosine N1-oxide, 5'-glucosyladenosine N1-oxide, 5'-adenosinme diphosphate N1-oxide, and 5'-adenosine triphosphate N1-oxide have an $LD_{50}$ of at least 1,000 mg/kg, respectively. Thus, these compounds are judged as substances safely administrable to humans.

Experiment 5

Volunteer Test 1

Using as subjects healthy males in their forties (seven males were randomly made as test subjects 1 to 5 and control subjects 1 and 2) except for suffering from moderate periodontal diseases (with a periodontal pocket depth of 3 mm or deeper but less than 6 mm) not requiring any acute treatment, the influences of five types of mouthwashes as test solutions 1 to 5, which had been prepared by adding any one of the ingredients as shown in the following Table 1 to refined water, dissolving the ingredients therein, and membrane filtering the resulting solutions; wherein the adenosine N1-oxide was the one obtained in Experiment 1, the 3'-glucosyladenosine N1-oxide and 5'-glucosyladenosine N1-oxide were those obtained in Experiment 2, and the 5'-adenosine diphosphate N1-oxide and 5'-adenosine diphosphate N1-oxide were those obtained in Experiment 3. As controls, control solutions 1 and 2 were similarly prepared as in the above test solutions except for using tranexamic acid or dipotassium glycyrrhizinate commonly used as representative medicinal ingredients for treating periodontal diseases, and subjected to the same test as above. For reference, tranexamic acid and dipotassium glycyrrhizinate are respectively incorporated into tooth pastes directed to prevent or treat periodontal diseases usually in an amount of about 0.05%.

In a questionnaire made before each test, every subject had been revealed to have a daily habit of brushing his teeth every after meal. To avoid any influence inherent to toothpastes used by the subjects on test results, a tooth powder with the following prescription, which had been previously prepared, was allocated to every subject for brushing his teeth.

<Prescription of Tooth Powder>

| | (%) |
|---|---|
| Aluminum hydroxide (submicron particle) | 90.5 |
| Aluminum hydroxide (325 mesh) | 6.0 |
| Sodium fluoride | 0.1 |
| Sodium lauryl sulfate | 1.8 |
| Saccharin | 0.2 |
| Flavour | 1.2 |
| Refined water | Quantity for completing the total mass to 100% |

Under respective lifestyle habits, the subjects were allowed to cleanse their oral cavities every after meal for six months in such a manner of allocating 200 mL of any one of the test solutions 1 to 5 and the control solutions 1 and 2 to the subjects 1 to 5 and the subjects 1 and 2, respectively; allowing to keep about 50 mL of any one of the allocated solutions for 30 seconds in their oral cavities; promptly allowing them to spit the solutions; and allowing the above procedures for cleansing their oral cavities to repeat four times in total. Except for directing every subject to avoid any gargling and eating/drinking just after the above procedures, they were allowed to spend their daily life according to their respective lifestyle habits. Symptoms of loose teeth on the day initiating the test and at the ends of two, four, and six months after initiating the test were evaluated by a dental hygienist under a doctor's guidance according to the following criteria. The following Table 1 shows the results.

<Criteria>

A: A distinct improvement in tooth mobility is observed on a tooth mobility test (or periodontometry) with a pincette compared with that before initiating the test;

B: Somewhat improvement in tooth mobility is observed on a tooth mobility test with a pincette compared with that before initiating the test; and C: No improvement or rather aggravation is observed on a tooth mobility test with a pincette compared with that before initiating the test.

TABLE 1

| Composition (% by mass) | Test solution 1 | Test solution 2 | Test solution 3 | Test solution 4 | Test solution 5 | Control solution 1 (Control) | Control solution 2 (Control) |
|---|---|---|---|---|---|---|---|
| Adenosine N1-oxide | 0.5 | 0 | 0 | 0 | 0 | 0 | 0 |
| 3-Glucosyl adenosine N1-oxide | 0 | 0.5 | 0 | 0 | 0 | 0 | 0 |
| 5'-Glucosyl adenosine N1-oxide | 0 | 0 | 0.5 | 0 | 0 | 0 | 0 |
| 5'-Adenosine diphosphate N1-oxide | 0 | 0 | 0 | 0.5 | 0 | 0 | 0 |
| 5'-Adenosine triphosphate N1-oxide | 0 | 0 | 0 | 0 | 0.5 | 0 | 0 |
| Tranexamic acid | 0 | 0 | 0 | 0 | 0 | 0.5 | 0 |
| Dipotassium glycyrrhizinate | 0 | 0 | 0 | 0 | 0 | 0 | 0.5 |
| Refined water | 99.5 | 99.5 | 99.5 | 99.5 | 99.5 | 99.5 | 99.5 |
| Total | 100 | 100 | 100 | 100 | 100 | 100 | 100 |

TABLE 1-continued

| Composition (% by mass) | Test solution 1 | Test solution 2 | Test solution 3 | Test solution 4 | Test solution 5 | Control solution 1 (Control) | Control solution 2 (Control) |
|---|---|---|---|---|---|---|---|
| Judgement on the day of initiating the test | Medium periodontal disease | Medium periodontal disease | Medium periodontal disease | Medium periodontal disease | Medium periodontal disease | Medium periodontal disease | Medium periodontal disease |
| Judgement at the end of two months after initiating the test | B | B | B | B | B | C | C |
| Judgement at the end of four months after initiating the test | A | B | B | B | B | C | C |
| Judgement at the end of six months after initiating the test | A | A | A | A | A | B | B |

As evident from Table 1, the subject with the test solution 1 gave a somewhat improvement in his tooth mobility by the tooth mobility test at the end of two months after initiating the test, compared with that on the day of initiating the test (Criterion B); and gave a distinct improvement in his tooth mobility on the test at the end of four months after initiating the test, compared with that tested on the day of initiating the test (Criterion A). Every subject with anyone of the test solutions 2 to 5 was judged as Criterion B at the end of two months after initiating the test, and still judged as Criterion B even at the end of four months after initiating the test; however, they were judged as Criterion A at the end of the six months after initiating the test. By contrast, every subject with any one of the control solutions 1 and 2 received no improvement or even an aggravation by the tooth mobility test at the end of two- and four-months after initiating the test (Criterion C), and they were still judged as Criterion B even at the end of six months after initiating the test.

These results show that adenosine N1-oxide, 3'-glucosyladenosine N1-oxide, 5'-glucosyladenosine N1-oxide, 5'-adenosine diphosphate N1-oxide, and 5'-adenosine triphosphate N1-oxide effectively improve periodontal diseases. In addition, their improvement effects were revealed to be distinctly higher than those of tranexamic acid and dipotassium glycyrrhizinate as controls. It was also revealed that adenosine N1-oxide has the highest improvement effect on periodontal diseases among these adenosine N1-oxide, 3'-glucosyladenosine N1-oxide, 5'-glucosyladenosine N1-oxide, 5'-adenosine diphosphate N1-oxide, and 5'-adenosine triphosphate N1-oxide.

Although Table 1 does not show, a dental hygienist under a doctor's guidance evaluated unpleasant breath induced by periodontal diseases for every subject with any of the test solutions 1 to 5 and the control solutions 1 and 2 at the end of six months after initiating the test, revealing that all the subjects with any of the test solutions 1 to 5 were distinctly improved in their unpleasant breath compared with those before initiating the test. In particular, the subject with the test solution 1 showed almost no unpleasant breath induced by periodontal diseases. While, the subjects with the control solutions 1 and 2 gave an unchanged or exacerbated symptom compared to those before initiating the test.

The experiment results show that adenosine N1-oxide and derivatives thereof are effective on the prevention and/or the treatment of periodontal diseases. Among adenosine N1-oxide, 3'-glucosyladenosine N1-oxide, 5'-glucosyladenosine N1-oxide, 5'-adenosine diphosphate N1-oxide, and 5'-adenosine triphosphate N1-oxide, adenosine N1-oxide has the highest improvement effect on periodontal diseases; however, 3'-glucosyladenosine N1-oxide, 5'-glucosyladenosine N1-oxide, 5'-adenosine diphosphate N1-oxide, and 5'-adenosine triphosphate N1-oxide, as well as adenosine N1-oxide, exert the desired effects in the present invention when used alone or in two or more combinations thereof. Compared to adenosine N1-oxide, since 3'-glucosyladenosine N1-oxide, 5'-glucosyladenosine N1-oxide, 5'-adenosine diphosphate N1-oxide, and 5'-adenosine triphosphate N1-oxide have a higher solubility in solvents such as water, they can be incorporated into the mouthwash composition for preventing and/or treating periodontal diseases of the present invention at a relatively higher concentration than that for adenosine N1-oxide.

Experiment 6

Volunteer Test 2

For adenosine N1-oxide, which had marked the highest improvement effect on periodontal diseases in Experiment 5, it was examined in more detail for its improvement action on periodontal diseases: Eight females, 20- to 30-year-old, as subjects, who were healthy except for suffering from medium periodontal diseases (with a periodontal pocket depth of 3 mm or deeper but less than 6 mm), were subjected to a volunteer test similarly as in Experiment 5 except for using six types of aqueous solutions containing 0.001 to 7.5% adenosine N1-oxide and setting a test period of seven months. The reason why the test period in this experiment was set to seven months longer than that in Experiment 5 by one month was to clearly determine the effect of adenosine N1-oxide at a lower concentration than that in Experiment 5 because there was also provided a system where adenosine N1-oxide was used at such a lower concentration than that in Experiment 5. As a control, a 5% aqueous solution of tranexamic acid (i.e., a control solution) was used.

In a questionnaire made before initiating the test, every subject was revealed to have a lifestyle habit of daily brushing her teeth every after meals and, under such a lifestyle habit, they were allowed to wash their oral cavities with 200 mL of any one of the test solutions 1 to 6 and the control solution for seven months similarly as in Experiment 5. The subjects were allowed to brush their teeth with the same toothpaste as used in Experiment 5. Except for directing them to avoid oral rinse and drinks/meals just after cleansing their oral cavities, they were allowed to spend their daily life as usual. Before initiating the test, a dental hygienist under a doctor's guidance evaluated the conditions of gingivitis for each subject at the end of seven months based on the same criteria as shown in Experiment 5. The results are in Table 2.

TABLE 2

| Composition (% by mass) | Test solution 1 | Test solution 2 | Test solution 3 | Test solution 4 | Test solution 5 | Test solution 6 | Control solution (Control) |
|---|---|---|---|---|---|---|---|
| Adenosine N1-oxide | 0.001 | 0.01 | 0.5 | 2.5 | 5 | 7.5 | 0 |
| Tranexamic acid | 0 | 0 | 0 | 0 | 0 | 0 | 5 |
| Refined water | 99.999 | 99.99 | 99.5 | 97.5 | 95 | 92.5 | 95 |
| Total | 100 | 100 | 100 | 100 | 100 | 100 | 100 |
| Judgement on the day of initiating the test | Medium periodonal disease | Medium periodonal disease | Medium periodonal disease | Medium periodonal disease | Medium periodonal disease | Medium periodonal disease | Medium periodonal disease |
| Judgement at the end of seven months after initiating the test | C | B | A | A | A | A | B |

As evident from Table 2, the subject with the test solution 1 showed no improvement or rather exacerbation in her tooth mobility at the end of seven months after initiating the test compared with the symptom at initiating the test (Criterion C). The subject with the test solution 2 showed a somewhat improvement in her tooth mobility compared with the symptom at initiating the test (Criterion B). The subjects with any one of the test solutions 3 to 6 showed a distinct improvement in their tooth mobility compared with their symptoms at initiating the test (Criterion A). By contrast, the subject with the control solution still remained to merely show a somewhat improvement in her tooth mobility at the end of seven months after initiating the test (Criterion B).

Similarly as in Experiment 5, the results in this experiment show that adenosine N1-oxide is distinctly effective on the prevention and/or the treatment of periodontal diseases: It was revealed that adenosine N1-oxide effectively prevents and/or treats periodontal diseases at concentrations of 0.01% or higher. In particular, adenosine N1-oxide distinctly, effectively prevents and/or treats periodontal diseases at concentrations in the range of 0.5% or higher. Also, 3'-glucosyladenosine N1-oxide, 5'-glucosyladenosine N1-oxide, 5'-adenosine diphosphate N1-oxide, and 5'-adenosine triphosphate N1-oxide as derivatives of adenosine N1-oxide have been revealed to be effective in preventing and/or treating periodontal diseases at concentrations of 0.01% or higher similar to adenosine N1-oxide when experimented similarly as in this experiment.

At the termination of the test, as not shown in Table 2, a dental hygienist under a doctor's guidance examined unpleasant breath induced by periodontal diseases in the subjects experimented with any one of the test solutions 1 to 6 and the control solution, revealing that every subject with any one of the test solutions 2 to 6 was distinctly improved in their unpleasant breath compared with those before initiating the test. By contrast, the subjects with the test solution 1 and the control solution gave an unchanged or exacerbated symptom as compared to those before initiating the test.

Based on the results in the above-mentioned Experiments 4 to 6, adenosine N1-oxide and derivatives thereof in themselves are safe substances against living bodies, and they are judged to be advantageously used as effective ingredients in mouthwash compositions for preventing and/or treating periodontal diseases. Also, such mouthwash compositions are judged to be effective in inhibiting unpleasant breath induced by periodontal diseases.

The following Examples explain the present invention in more detail but they should not limit the scope of the present invention.

Example 1

Mouthwash

Mouth Rinse

The following ingredients shown in the prescription below were mixed, dissolved, microfiltered, and injected into a sterilized vessel to obtain a mouthwash according to the present invention.

<Prescription>

| | (%) |
|---|---|
| Ethanol | 15 |
| Adenosine N1-oxide obtained by the method in Experiment 1 | 2 |
| Polyoxyethylene hydrogenated castor oil | 2 |
| Sodium benzoate | 0.05 |
| Sodium dihydrogen phosphate | 0.1 |
| Colorant | 0.1 |
| Flavour | 0.03 |
| Refined water | Quantity for completing the total mass to 100% |

Since the product effectively prevents and/or treats periodontal diseases, it can be advantageously used in the maintenance/promotion of oral health. In use, the product can be used intact or after diluting with water by 2- to 200-folds, and 50 to 300 mL of which is used to cleanse a subject's oral cavity between or after meals for attaining the prevention and/or the treatment of periodontal diseases effectively. Also, the product exerts an effect on the prevention of unpleasant breath induced by periodontal diseases.

Example 2

Mouthwash

Mouth Rinse

The following ingredients shown in the prescription below were mixed, dissolved, microfiltered, and injected into sterilized vessels to obtain two types of mouthwashes according to the present invention containing the 3'-glucosyladenosine N1-oxide or 5'-glucosyladenosine N1-oxide obtained by the method in Experiment 2.
<Prescription>

|  | (%) |
|---|---|
| 3'-Glucosyladenosine N1-oxide or 5'-glucosyladenosine N1-oxide obtained by the method in Experiment 2 | 1 |
| Polyvinyl pyrrolidone | 65 |
| Sodium polyacrylate | 20 |
| Glycyrrhizin | 0.01 |
| Refined water | Quantity for completing the total mass to 100% |

Since the products easily penetrate into periodontal pockets, they can be advantageously used in preventing and/or treating periodontal diseases. In use, the products can be used intact or after diluted with water by 2- to 100-folds, and 50 to 300 mL of any of which is used to cleanse a subject's oral cavity between or after meals for attaining the prevention and/or the treatment of periodontal diseases effectively. Also, the products exert an effect on the prevention of unpleasant breath induced by periodontal diseases.

Example 3

Chewing Gum Agent

The following ingredients shown in the prescription below were mixed, kneaded, and packaged to obtain two types of chewing gum agents according to the present invention, which contain the adenosine N1-oxide obtained by the method in Experiment 1 and the 5'-adenosine diphosphate N1-oxide or 5'-adenosine triphosphate N1-oxide obtained in Experiment 3 as effective ingredients for preventing and/or treating periodontal diseases.
<Prescription>

|  | (%) |
|---|---|
| Adenosine N1-oxide obtained by the method in Experiment 1 | 1.5 |
| 5'-Adenosine diphosphate N1-oxide or 5'-adenosine triphosphate N1-oxide obtained by the method in Experiment 3 | 0.5 |
| Gum base | 86.98 |
| Xylitol | 10 |
| Sucralose | 0.01 |
| Aspartame | 0.01 |
| Flavour | 1 |

The products are useful as chewing gum agents for preventing unpleasant breath induced by periodontal diseases and for maintaining/promoting oral health, as well as for preventing and/or treating periodontal diseases.

Example 4

Toothpaste

The following ingredients shown in the prescription below were mixed, kneaded, sterilized by heating, and injected into sterilized vessels to obtain totally four types of toothpastes according to the present invention, which contain the adenosine N1-oxide obtained by the method in Experiment 1, the 3'-glucosyladenosine N1-oxide or 5'-glucosyladenosine N1-oxide obtained by the method in Experiment 2, and the 5'-adenosine diphosphate N1-oxide or 5'-adenosine triphosphate N1-oxide obtained by the method in Experiment 3 as effective ingredients for preventing and/or treating periodontal diseases.
<Prescription>

|  | (%) |
|---|---|
| Adenosine N1-oxide obtained by the method in Experiment 1 | 3 |
| 3'-Glucosyladenosine N1-oxide or 5'-glucosyladenosine N1-oxide obtained by the method in Experiment 2 | 3 |
| 5'-Adenosine diphosphate N1-oxide or 5'-adenosine triphosphate N1-oxide obtained by the method in Experiment 3 | 3 |
| Dicalcium phosphate | 50 |
| Sodium lauryl sulphate | 1.5 |
| Xylitol | 26 |
| Polyoxyethylene sorbitan laurate | 0.5 |
| Saccharine sodium | 0.05 |
| Refined water | Quantity for completing the total mass to 100% |

These products are useful as toothpastes for preventing unpleasant breath induced by periodontal diseases and for maintaining/promoting oral health, as well as for preventing and/or treating periodontal diseases.

Example 5

Troche

The following ingredients shown in the prescription below were mixed, kneaded, tabletted, and packaged to obtain totally four types of troches according to the present invention, which contain the adenosine N1-oxide obtained by the method in Experiment 1, the 3'-glucosyladenosine N1-oxide or 5'-glucosyladenosine N1-oxide obtained by the method in Experiment 2, and the 5'-adenosine diphosphate N1-oxide or 5'-adenosine triphosphate N1-oxide obtained by the method in Experiment 3, as effective ingredients for preventing and/or treating periodontal diseases.
<Prescription>

|  | Part by mass |
|---|---|
| Adenosine N1-oxide obtained by the method in Experiment 1 | 30 |
| 3'-Glucosyladenosine N1-oxide or 5'-glucosyladenosine N1-oxide obtained by the method in Experiment 2 | 30 |

-continued

| | Part by mass |
|---|---|
| 5'-Adenosine diphosphate N1-oxide or 5'-adenosine triphosphate N1-oxide obtained by the method in Experiment 3 | 30 |
| Xylitol | 130 |
| Menthol | 130 |
| Talc | 50 |
| Magnesium stearate | 100 |
| Acesulfam K | 0.01 |
| Licorice root extract | 0.01 |
| Refined water | q.s. |

These products are useful as troches for preventing unpleasant breath induced by periodontal diseases and for maintaining/promoting oral health, as well as for preventing and/or treating periodontal diseases.

Example 6

Mouthwash

Mouth Rinse

Two types of mouthwashes were prepared similarly as in Example 1 except for replacing the adenosine N1-oxide as shown in the prescription in Example 1 with the 3'-glucosyladenoisne N1-oxide or 5'-glucosyladenosine N1-oxide obtained by the method in Experiment 2.

The products are useful as mouthwashes for preventing unpleasant breath induced by periodontal diseases and for maintaining/promoting oral health, as well as for preventing and/or treating periodontal diseases.

Example 7

Mouthwash

Mouth Rinse

Eight types of mouthwashes were prepared similarly as in Example 2 except for replacing the glycyrrhizin shown in the prescription in Example 2 with saccharine, saccharine sodium, aspartame, acesulfam K, sucralose, licorice extract, steviol glycoside, or thaumatin.

These products are useful as mouthwashes for preventing unpleasant breath induced by periodontal diseases and for maintaining/promoting oral health, as well as for preventing and/or treating periodontal diseases.

INDUSTRIAL APPLICABILITY

The mouthwash composition for preventing and/or treating periodontal diseases of the present invention is industrially, distinctly useful as a mouthwash composition for safely and effectively preventing and/or treating periodontal diseases that have been recently increasing in morbidity along with affected individuals among increasingly younger people.

The invention claimed is:

1. A method for preventing and/or treating periodontal diseases, which comprises a step of administering a composition to the oral cavity of a subject in need thereof to cleanse the oral cavity;
   said composition comprising:
   (i) one or more members selected from the group consisting of adenosine N1-oxide (CAS No. 146-92-9), 3'-glucosyladenosine N1-oxide, 5'-glucosyladenosine N1-oxide, 5'-adenosine diphosphate N1-oxide, and 5'-adenosine triphosphate N1-oxide as an effective ingredient(s); and
   (ii) a carrier
   wherein said composition does not contain any saccharide assimilable by periodontal disease bacteria; and
      whereby unpleasant breath induced by periodontal diseases is improved and oral health is maintained and/or promoted.

2. The method of claim 1, wherein said composition further contains a high intensity sweetener as a sweetener.

3. The method of claim 2, wherein said high intensity sweetener is one or more members selected form the group consisting of saccharine, saccharine sodium, aspartame, acesulfam-K, sucralose, licorice extract, steviol glycoside, thaumatin, and glycyrrhizin.

4. The method of claim 1, wherein said composition is in the form of a product selected from the group consisting of mouthwashes, toothpastes, tooth powders, chewing gum agents, and troches.

5. The method of claim 1, wherein said composition further comprising one or more ingredients selected from the group consisting ot tranexamic acid, tranexamic acid hydrochloride, dipotassium glycyrrhizinate, α-glycyrrhetinic acid, dihydrocholesterol, minocycline hydrochloride, chlorhexidine, chlorhexidine hydrochloride, thymol, methyl salicylate, catechin, povidone-iodine, benzalkonium chloride, cetylpyridinium chloride, cetylpyridinium chloride hydrate, alkyl di(aminoethyl)glycin, dequalinium chloride, lysozyme hydrochloride, tocopherol hydrochloride, sodium azulene sulfonate hydrate, triclosan, allantoin, allantoin chlorohydroxy aluminum, monocalcium phosphate, dicalcium phosphate, and tribasic calcium phosphate.

* * * * *